(12) United States Patent
Coleman et al.

(10) Patent No.: US 7,141,242 B2
(45) Date of Patent: Nov. 28, 2006

(54) HEPATITIS B VIRUS SURFACE ANTIGEN MUTANT AND METHODS OF DETECTION THEREOF

(75) Inventors: Paul F. Coleman, Lindenhurst, IL (US); Isa K. Mushahwar, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/847,493

(22) Filed: May 17, 2004

(65) Prior Publication Data

US 2004/0209248 A1    Oct. 21, 2004

Related U.S. Application Data

(62) Division of application No. 09/821,877, filed on Mar. 30, 2001.

(51) Int. Cl.
*A61K 39/29* (2006.01)
*G01N 33/53* (2006.01)

(52) U.S. Cl. .................. 424/189.1; 435/975; 435/5; 530/350; 530/826

(58) Field of Classification Search ................ 530/350, 530/826; 435/5, 7.1, 810, 975; 424/198.1, 424/189.1
See application file for complete search history.

(56) References Cited

U.S. PATENT DOCUMENTS 5,464,933 A    11/1995   Bolognesi et al.
5,593,825 A    1/1997    Carman et al.
5,595,739 A    1/1997    Carman et al.
5,925,512 A    7/1999    Carman et al.
6,172,193 B1 * 1/2001   Primi et al. ................. 530/350

OTHER PUBLICATIONS

Coleman et al., Journal of Medical Virology 59: 19-24 (1999).*
Coleman P, Emerging Infectious Diseases 2006, Feb. 12, No. 2, pp. 1-10.*
Lai et al. Nucleic acids Research, 1991, vol. 19, No. 18, pp. 5078.*
Hepatitis B surface antigen seqeunces published on Jan. 4, 2006 by NCBI: Q773S4, AAO12662, Q67886, AAT28717, 28718, and AAT28719.*
Carman, et al., *Gastroenterology*, Gentic Variation in Hepatitis B Virus, 102:711-719 (1992).
Carman, et al., *Lancet*, Viral Genetic Variation: Hepatitis B Virus as a Clinical Example, 341:349-353 (1993).
Courouce, et al., *Bibliotheca Haematologica*, The a(w) Subdeterminantst, 42:31-41 (1976).
Gerlich, et al., *In Viral Hepatitis and Liver Disease*, Functions of Hepatitis B Virus Proteins and Virus Assembly, Holinger, et al.,., eds. Williams-Wilkens, Baltimore, MD, 121-134 (1991).
Okamoto, et al., *Pediatric Research*, Mutations Within the S Gene of Hepatitis B Virus Transmitted from Mothers to Babies Immunized with Hepatitis B immune Globulin and Vaccine, 32:264-268 (1992).
Tiollais, et al., *Nature*, The Hepatitis B Virus, 317:489-495 (1985).

* cited by examiner

*Primary Examiner*—Bao Qun Li
(74) *Attorney, Agent, or Firm*—Cheryl L. Becker

(57) ABSTRACT

The subject invention relates to a novel hepatitis B surface antigen mutant and methods of detecting this mutant, and/or antibodies thereto, in patient samples. In particular, the mutant contains a substitution of amino acid threonine for the amino acid alanine at position 123 in the amino acid sequence of the hepatitis B surface antigen (HBsAg) protein.

3 Claims, 7 Drawing Sheets

Nucleotide sequence of the entire envelope gene for the mutant HBsAg strain:

ATGGGGCAGAATCTTTCCACCAGCAATCCTCTGGGATTCTTTCCCGACCACCAGTTGGAT

CCAGCCTTCAGAGCAAACACCAACAATCCAGATTGGGACTTCAATCCCAACAAGGACAC

CTGGCCAGACGCCAACAAGGTAGGAGCTGGAGCATTCGGACTGGGGTTCACCCCACCGC

ACGGAGGCCTTTTGGGGTGGAGCCCTCAGGCTCAGGGCATAACACAAACCTTGCCAGCA

AATCCGCCTCCTGCTTCCACCAATCGCCAGTCAGGAAGGCAGCCTACCCCGCTGTCTCCA

CCTTTGAGAAACACTCATCCTCAAGCCATGCAGTGGAACTCCACAACTTTCCACCAAACT

CTGCAAGATCCCAGAGTGAGAGGTCTGTATTTCCCTGCTGGTGGCTCCAGTTCAGGAACAG

TAAACCCTGTTCCGACTACTGTCTCTCCCATATCGTCAATCTTCTCGAGGATTGGGGACC

CTGCGCGGAACATGGAGAACATCACATCAGGATTCCTAGGACCCCTGCTCGTGTTACAG

GCGGGGTTTTTCTTGTTGACAAGAATCCTCACAATACCGCAGAGTCTAGACTCGTGGTG

GACTTCTCTCAATTTTCTAGGGGGAACTACCGTGTGTCTTGGCCAAAATTCGCAGTCCC

CAACCTCCAATCACTCACCAACCTCCTGTCCTCCAACTTGTCCTGGTTATCGCTGGATGT

GTCTGCGGCGTTTTATCATCTTCCTCTTCATCCTGCTGCTATGCCTCATCTTCTTGTTGGT

TCTTCTGGACTATCAAGGTATGTTGCCCGTTTGTCCTCTAATTCCAGGATCTTCAACCAC

CAGCACGGGACCATGCAGAGCCTGCACGACTCCTGCTCAAGGAACCTCTATGTATCCCT

CCTGTTGCTGTACAAAACCTTCGGATGGAAACTGCACCTGTATTCCCATCCCATCATCCT

GGGCTTTCGGAAAATTCCTATGGGAGTGGGCCTCAGCCCGTTTCTCCTGGCTCAGTTTAC

TAGTGCCATTTGTTCAGTGGTTCGTAGGGCTTTCCCCCACTGTTTGGCTTTCAGTTATATG

GATGATGTTGTACTGGGGGCCAAGTCTGTACACCATCTTGAGTCCCTTTTTACCGCTGTT

ACCAATTTTCTTTTGTCTTTGGGTATACATTTAAACCCTAATAAA

FIG.1

Amino acid sequence of the entire envelope gene for the mutant HBV strain:

[preS1]MGQNLSTSNPLGFFPDHQLDPAFRANTNNPDWDFNPNKDTWPDANKVGAGAFGL
GFTPPHGGLLGWSPQAQGITQTLPANPPPASTNRQSGRQPTPLSPPLRNTHPQA

[preS2]MQWNSTTFHQTLQDPRVRGLYFPAGGSSSGTVNPVPTTVSPISSIFSRIGDPARN

[S]$M_1$ENITSGFLG$_{10}$PLLVLQAGFF$_{20}$LLTRILTIPQ$_{30}$SLDSWWTSLN$_{40}$FLGGTTVCLG$_{50}$QNSQS

PTSNH$_{60}$SPTSCPPTCP$_{70}$GYRWMCLRRF$_{80}$IIFLFILLLC$_{90}$LIFLLVLLDY$_{100}$QGMLPVCPLI$_{110}$PGS

STTSTGP$_{120}$CR$\underline{A}$CTTPAQG$_{130}$TSMYPSCCCT$_{140}$KPSDGNCTCI$_{150}$PIPSSWAFGK$_{160}$FLWEWASA RF$_{170}$SWLSLLVPFV$_{180}$QWFVGLSPTV$_{190}$WLSVIWM$\underline{L}$Y$_{200}$WGPSLY$\underline{I}$ILS$_{210}$PFLPLLPIFF$_{220}$CL

WVYI.

subtype ayw2, genotype D

Three S substitutions found:

1.) Thr to Ala 123 (affects H166 epitope)
2.) Trp to Leu 199 (outside "a" determinant)
3.) Ser to Thr 207 (outside "a" determinant)

FIG.2

Nucleotide sequence of the small envelope gene for wild type HBV ayw$_2$:

ATGGAGAACATCACATCAGGATTCCTAGGACCCCTGCTCGTGTTACAGGCGGGGTTTT

TCTGGTTGACAAGAATCCTCACAATACCGCAGAGTCTAGACTCGTGGTGGACTTCTCTC

AATTTTCTAGGGGGAACTACCGTGTGTCTTGGCCAAAATTCGCAGTCCCCAACCTCCAA

TCACTCACCAACCTCCTGTCCTCCAACTTGTCCTGGTTATCGCTGGATGTGTCTGCGGC

GTTTTATCATCTTCCTCTTCATCCTGCTGCTATGCCTCATCTTCTTGTTGGTTCTTCTGGA

CTATCAAGGTATGTTGCCCGTTTGTCCTCTAATTCCAGGATCATCAACCACCAGCACGG

GACCCTGCAGAACCTGCACGACTCCTGCTCAAGGAACCTCTATGTATCCCTCCTGTTGC

TGTACAAAACCTTCGGATGGAAACTGCACCTGTATTCCCATCCCATCATCCTGGGCTTT

CGGAAAATTCCTATGGGAGTGGGCCTCAGCCCGTTTCTCTTGGCTCAGTTTACTAGTGC

CATTTGTTCAGTGGTTCGTAGGGCTTTCCCCCACTGTTTGGCTTTCAGTTATATGGATGA

TGTGGTATTGGGGGCCAAGTCTGTACAGCATCTTGAGTCCCTTTTTACCGCTGTTACCA

ATTTTCTTTTGTCTTTGGGTATACATTTAA

FIG.3

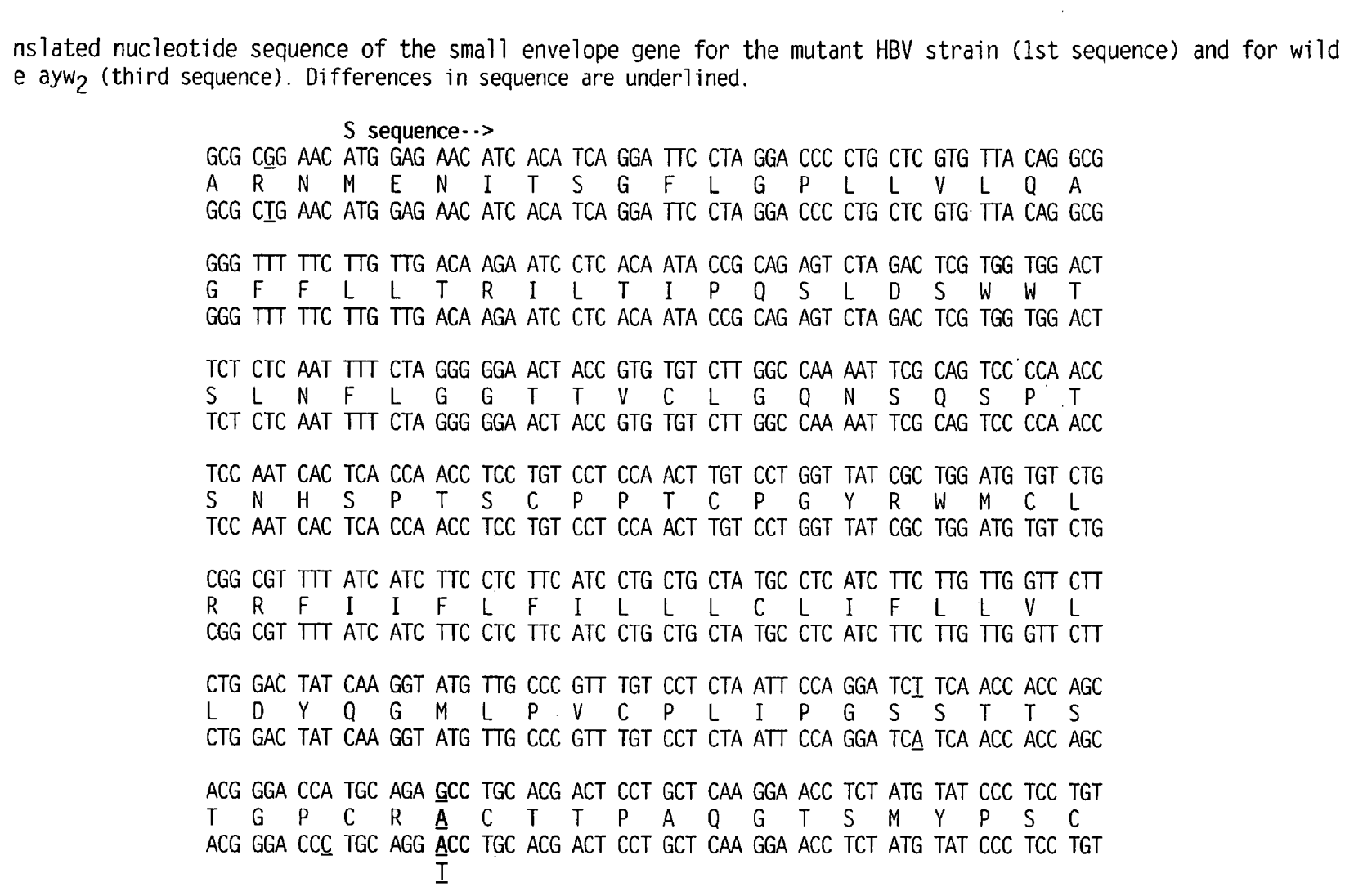

Translated nucleotide sequence of the small envelope gene for the mutant HBV strain (1st sequence) and for wild type ayw₂ (third sequence). Differences in

```
TGC TGT ACA AAA CCT TCG GAT GGA AAC TGC ACC TGT ATT CCC ATC CCA TCA TCC TGG GCT
 C   C   T   K   P   S   D   G   N   C   T   C   I   P   I   P   S   S   W   A
TGC TGT ACA AAA CCT TCG GAT GGA AAC TGC ACC TGT ATT CCC ATC CCA TCA TCC TGG GCT

TTC GGA AAA TTC CTA TGG GAG TGG GCC CGT TTC TCC TGG CTC AGT TTA CTA GTG
 F   G   K   F   L   W   E   W   A   R   F   S   W   L   S   L   L   V
TTC GGA AAA TTC CTA TGG GAG TGG GCC CGT TTC TCT TGG CTC AGT TTA CTA GTG

CCA TTT GTT CAG TGG TTC GTA GGG CTT TCC CCC ACT GTT TGG CTT TCA GTT ATA TGG ATG
 P   F   V   Q   W   F   V   G   L   S   P   T   V   W   L   S   V   I   W   M
CCA TTT GTT CAG TGG TTC GTA GGG CTT TCC CCC ACT GTT TGG CTT TCA GTT ATA TGG ATG

ATG TAC TGG GGG CCA AGT CTG TAC ACC ATC TTG AGT CCC TTT TTA CCG CTG TTA CCA
 M   Y   W   G   P   S   L   Y   T   I   L   S   P   F   L   P   L   L   P
ATG TAC TGG GGG CCA AGT CTG TAC AGC ATC TTG AGT CCC TTT TTA CCG CTG TTA CCA
                                 S

ATT TTC TTT TGT CTT TGG GTA TAC ATT TAA
 I   F   F   C   L   W   V   Y   I
ATT TTC TTT TGT CTT TGG GTA TAC ATT TAA
```

FIG. 4B

Nucleotide sequence 492 to 675 encoding the "a" determinant for the mutant HBV strain.

$T_{492}$AT CAA GGT ATG TTG CCC GTT TGT CCT CTA ATT CCA GGA TCT TCA ACC ACC AGC ACG GGA CCA TGC AGA $G_{561}$CC TGC ACG ACT CCT GCT CAA GGA ACC TCT ATG TAT CCC TCC TGT TGC TGT ACA AAA CCT TCG GAT GGA AAC TGC ACC TGT ATT CCC ATC CCA TCA TCC TGG GCT TTC GGA AAA$_{675}$

FIG.5

Amino acid sequence of the "a" determinant for the mutant HBV strain:

$Y_{100}$QGMLPVCPLI$_{110}$PGSSTTSTGP$_{120}$CRACTTPAQG$_{130}$TSMYPSCCCT$_{140}$ KPSDGNCTCI$_{150}$PIPSSWAFGK$_{160}$

HEPATITIS B VIRUS SURFACE ANTIGEN MUTANT AND METHODS OF DETECTION THEREOF

The subject application is a divisional of pending U.S. Pat. application Ser. No. 09/821,877, filed on Mar. 30, 2001, which is hereby incorporated in its entirety by reference.

BACKGROUND OF THE INVENTION

1. Technical Field

The subject invention relates to a novel hepatitis B surface antigen mutant and methods of detecting this mutant, and/or antibodies thereto, in patient samples. In particular, the mutant contains a substitution of amino acid threonine for the amino acid alanine at position 123 in the amino acid sequence of the hepatitis B surface antigen (HBsAg) protein.

2. Background Information

The hepatitis B virus (HBV) is known to cause a variety of disease states from mild subclinical infection to chronic active and fulminant hepatitis. The genome of the virus is a circular, partially double stranded DNA sequence of approximately 3200 basepairs which code for at least six different viral genes (Tiollais et al., Nature 317:489–495 (1985)). More specifically, the polymerase gene overlaps the envelope gene and also partially overlaps the X and core genes. The product of the envelope gene consists of three proteins which have different initiation sites but the same termination site. These three proteins (i.e., small (S), middle (M), and large (L) HBsAg) all contain the S-HBsAg gene sequence of 226 amino acids (Gerlich et al. in Viral Hepatitis and Liver Disease, Hollinger et al., eds., Williams-Wilkens, Baltimore, Md., pages 121–134 (1991)). The M-HBsAg contains the 55 amino acid PreS2 sequence and the S sequence for a total length of 281 amino acids. The L-HBsAg protein contains the 108 amino acid PreS1 sequence plus the PreS2 and S sequences for a total length of 389 amino acids. In addition, each of the three envelope proteins exhibit different degrees of glycosylation.

The core gene encodes the nucleocapsid protein, hepatitis B core antigen (HBcAg). Immediately upstream of the core gene is the precore region. The first 19 amino acids of the precore region serve as a signal for membrane translocation and eventual secretion of the precore gene product, the hepatitis B e antigen (HBeAg).

Similar to the Human Immunodeficiency Virus (HIV), HBV uses reverse transcriptase (RT) as an essential step in the replication cycles. However, RT has poor proofreading ability, thereby leading to a high rate of nucleotide misincorporation. Calculations suggest that this error-prone replication leads to one point replacement, deletion or insertion per 1000 to 100,000 nucleotides copied (Carman et al., Lancet 341:349–353 (1993)). Variability in HBV surface antigen was first described using classical subtyping studies Courouce et al., Bibliotheca Haematologica 42:1 (1976)).

The HBV envelope regions encompassing PreS1 and PreS2 and the "a" determinant are exposed on the surface of the viral particle and are therefore expected to be targets of immune surveillance (Gerlich et al., supra). Some surface antigen mutants previously described have significantly affected the antigenicity of the "a" determinant which contains both common and group-specific determinants (Carman et al., Gastroenterology 102:711–719 (1992)). The "a" determinant is located between amino acids 100–160 of S-HBsAg and presents a complex conformational epitope which is stabilized by disulfide bonding between highly conserved cysteine residues. The "a" determinant immunoreactivity can be partially mimicked using cyclic synthetic peptides. Further, although the "a" determinant had been traditionally defined by reactivity to polyclonal antisera, the use of monoclonal antibody has shown that the "a" determinant consists of at least five partially overlapping epitopes (Peterson et al., J. Immunol. 132:920–927 (1984)). The most common surface antigen mutant described in the literature is a single nucleotide substitution leading to the substitution of glycine at amino acid position 145 of S-HBsAg with arginine (G-R 145). This G-R 145 mutation destroys some, but not all, "a" determinant epitopes.

Additionally, other mutations in the "a" determinant result in loss of subtypic or type-specific determinants y/d and w/r. Also the emergence of gross deletions and point mutations in the PreS1/PreS2 region suggest that the product of the envelope gene is under immune selection in chronically infected patients. Further, HBV mutants which cannot replicate because of deletions in the env, C or P genes have been noted in plasma from HBV carriers. All co-exist with HBV forms which are replication competent.

Okamoto et al. have demonstrated that mutant genomes with gross deletions in the PreS/S, C and P genes derived from plasma or asymptomatic carriers may be complemented in transient expression systems with hepatoma cells (Okamoto et al., Pediatric Research 32:264–268 (1992)). In fact, the suggestion has been made that HBV mutants acting as defective interfering particles may attenuate wildtype virus replication and thereby help maintain persistence of the invention.

In view of the above, the isolation of Hepatitis B surface antigen mutants is certainly advantageous. Furthermore, new mutants may arise over time due to vaccine administration and/or infection. The identification and detection of mutant Hepatitis B viruses may thus lead to improved vaccine development and to detection systems which determine the presence of these mutants in patient samples.

All U.S. patents and publications are herein incorporated in their entirety by reference.

SUMMARY OF THE INVENTION

The present invention includes an isolated nucleotide sequence having at least 70% identity to SEQ ID NO:1 or to a fragment of said sequence which specifically hybridizes to the complement of SEQ ID NO:1.

Additionally, the present invention includes an isolated nucleotide sequence comprising a nucleotide sequence encoding a mutant hepatitis B surface antigen (HBsAg) "a" determinant in which the mutation is the substitution of the amino acid Ala for the amino acid Thr at position 123 of the isolated nucleotide sequence. The present invention also encompasses purified polypeptides encoded by the isolated nucleotide sequences described above as well as a purified polypeptide having at least 70% identity to SEQ ID NO:2.

Furthermore, the present invention includes a vector comprising one or more of the isolated nucleotide sequences described above as well as a host cell comprising this vector.

Additionally, the present invention includes a method for producing a polypeptide comprising a modified HBV "a" determinant comprising the steps of incubating the host cell, described above, for a time and under conditions sufficient for expression of the polypeptide.

Also, the present invention encompasses an antibody which binds to a mutant HBsAg "a" determinant and does not cross-react with the native HBsAg "a" determinant, wherein the mutation of the mutant "a" determinant is the substitution of the amino acid Ala for the amino acid Thr at position 123 of the HBsAg sequence.

The present invention also includes an isolated mutant hepatitis B virus, wherein the virus has a modified HBsAg "a" determinant comprising a substitution of the amino acid Ala for the amino acid Thr at position 123 of the HBsAg sequence. Also, the present invention includes a tissue culture-grown cell infected with this mutant virus.

Additionally, the present invention includes an immunogenic composition comprising the isolated virus described above or any one or more of the polypeptides described above.

The present invention also encompasses a polynucleotide probe comprising a Hepatitis B Virus genomic sequence encoding a modified HBsAg "a" determinant, wherein the modified HBsAg "a" determinant results from substitution of alanine for guanine at position 561 of the nucleotide sequence of the Hepatitis B Virus. The genomic sequence encoding the modified HBsAg "a" determinant may comprise SEQ ID NO:1.

Also, the present invention includes a kit for determining the presence of mutant HBV polynucleotides comprising the polynucleotide probe, described above, and a container. The invention also includes a kit for determining the presence of mutant hepatitis B surface antigen or antibody comprising a container containing the antibody described above. Additionally, the present invention encompasses a kit for determining the presence of mutant hepatitis B virus antigen or antibody comprising a container and any one of the polypeptides described above.

The present invention includes a method for detecting mutant HBV nucleic acids in a test sample comprising the steps of: (a) reacting a test sample suspected of containing mutant HBV nucleic acids with the probe described above under conditions and for a time sufficient to allow formation of a probe/mutant HBV nucleic acid complex; and (b) detecting the complex, presence of the complex indicating presence of mutant HBV nucleic acids in the sample.

Also, the present invention includes a method for detecting HBV antibodies in a test sample comprising the steps of: (a) contacting a test sample suspecting of containing the antibodies with any one or more of the polypeptides described above for a time and under conditions sufficient to allow formation of antibody/polypeptide complexes; and (b) detecting the antibody/polypeptide complexes, presence of the complexes indicating presence of the antibodies in the test sample.

Furthermore, the present invention includes a method for detecting mutant hepatitis B surface antigen (HBsAg) "a" determinant in a test sample comprising the steps of (a) reacting a test sample suspecting of containing mutant HBsAg "a" determinant with the antibody described above for a time and under conditions sufficient to allow formation of antigen/antibody complexes; and (b) detecting the antigen/antibody complexes, presence of the complexes indicating presence of mutant hepatitis B surface "a" determinant in the test sample. This method may further comprise the steps of: (c) contacting the antigen/antibody complexes with a conjugate comprising a second antibody attached to a signal-generating compound capable of generating a detectable signal for a time and under conditions sufficient to allow the formation of second antibody/antigen/antibody complexes; and (d) detecting presence of the signal generated by the signal-generating compound, presence of the signal indicating presence of the mutant hepatitis B surface antigen (HBsAg) "a" determinant in the test sample.

The present invention also encompasses an isolated nucleotide sequence having at least 70% identity to SEQ ID NO:4 (i.e., the nucleotide sequence of the "a" determinant of the mutant virus) or to a fragment of the sequence which specifically hybridizes to the complement of SEQ ID NO:4. Additionally, the invention includes a purified polypeptide encoded by this isolated nucleotide sequence as well as a vector comprising this isolated nucleotide sequence and a host cell comprising this vector.

Furthermore, the invention includes a purified polypeptide having at least 70% identity to SEQ ID NO:5.

BRIEF DESCRIPTION OF THE DRAWINGS

FIG. 1 illustrates the nucleotide sequence of the full envelope gene isolated from the mutant HBV virus of the present invention (SEQ ID NO:1). The nucleotide sequence of the mutant "a" determinant is represented by bases 492–675 of the full length envelope sequence.

FIG. 2 illustrates the amino acid sequence of the full length mutant HBsAg envelope protein (SEQ ID NO:2).

FIG. 3 represents the nucleic acid sequence of the small HBsAg envelope protein for subtype ayw$_2$ wildtype HBV virus (SEQ ID NO:3).

FIG. 4 represents the nucleotide sequence alignment of the mutated small envelope protein gene of the isolated HBV ayw$_2$ mutant, i.e. the 1st DNA sequence of SEQ ID NO: 6 with that of wild type HBV ayw$_2$, i.e. the 2nd DNA sequence of SEQ ID NO: 7, and the translated amino acid sequence (SEQ ID NO: 8) of said mutated small envelope protein gene.

FIG. 5 illustrates the nucleotide sequence of the mutant "a" determinant (i.e., bases 492–675 of the full length envelope sequence)(SEQ ID NO:4). The "a" determinant is between amino acids 100–160 of S (small) HBsAg.

FIG. 6 illustrates the corresponding polypeptide sequence of the mutant "a" determinant encoded by the nucleotide sequence shown in FIG. 5 (i.e., amino acids 100–160 of the S (small) HBsAg protein sequence)(SEQ ID NO:5).

DETAILED DESCRIPTION OF THE INVENTION

The subject invention relates to a novel mutant of hepatitis B virus (HBV) which has a modified "a" determinant as a result of an amino acid substitution (i.e., Thr to Ala) at amino acid position 123 of the S-HBsAg sequence. This amino acid substitution corresponds to a nucleotide substitution in the threonine codon of adenine to guanine at position 521 in the HBV genome.

In particular, the present invention includes the isolated nucleotide sequence of SEQ ID NO:1 which encodes the full envelope gene sequence of the mutant virus. Additionally, the present invention includes an isolated nucleotide sequence which corresponds to the "a" determinant sequence of the virus (SEQ ID NO:4), as well as the isolated nucleotide sequence of the full mutant virus. The invention also includes nucleotide sequences having at least 70% identity, preferably at least 80% identity, and more preferably at least 90% identity to the nucleotide sequences of the present invention, as well as complements thereof.

"Identity" is defined as the degree of sameness, correspondence or equivalence between the same strands (either sense or antisense) of two DNA segments. More specifically, sequence identity or percent identity is the number of exact matches between two aligned sequences divided by the length of the shorter sequence and multiplied by 100. The greater the percent identity, the higher the correspondence, sameness of equivalence between the two strands. An approximate alignment for nucleic acid sequences is provided by the local homology algorithm of Smith and Waterman, *Advances in Applied Mathematics* 2:482–489 (1981). This algorithm may be extended to use with peptide or protein sequences (in terms of identity or similarity) using the scoring matrix created by Dayhoff, *Atlas of Protein Sequences and Structure*, M. O. Dayhoff ed., 5 suppl. 3:353–358, National Biomedical Research Foundation, Washington, D.C., USA, and normalized by Gribskov, *Nucl. Acids Res.* 14(6):6745–66763 (1986). An implementation of this algorithm for nucleic acid and peptide sequences is provided by the Genetics Computer Group (Madison, Wis.) in the BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

"Complementarity" is defined as the degree of relatedness between two DNA segments. It is determined by measuring the ability of the sense strand of one DNA segment to hybridize with the antisense strand of the other DNA segment, under appropriate conditions, to form a double helix. In the double helix, wherever adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of two DNA segments.

The invention also includes the polypeptides encoded by the nucleotide sequences described above. In particular, the invention encompasses the polypeptide encoded by the isolated nucleotide sequence of the envelope gene comprising the nucleotide sequence of the "a" determinant of HBsAg of the mutant virus, polypeptides having at least 70% similarity to these amino acid sequences, preferably at least 80% similarity thereto, and more preferably at least 90% similarity thereto. Additionally, the invention includes the polypeptide sequence encoded by the nucleotide sequence of the mutant "a" determinant and the full mutant virus. The present invention also includes fragments of these sequences.

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. ("Identity" between two amino acid sequences is defined as the presence of a series of exactly alike or invariant amino acid residues of both sequences.) Percent similarity is calculated between the compared polypeptide sequences using programs known in the art (see above).

For purposes of the present invention, a "fragment" of a nucleotide sequence is defined as a contiguous sequence of approximately at least about 6, preferably at least about 8, more preferably at least about 10–12 nucleotides, and even more preferably at least about 15–18 nucleotides corresponding to a region of the specified nucleotide sequence.

Additionally, the present invention includes the isolated nucleotide sequence encoding the complete surface antigen or protein of the HBV mutant virus, the complement thereof, as well as fragments of the sequence and its complement.

The present invention also encompasses isolated nucleotide sequences having 70% identity, preferably 80% identity, and more preferably at least 90% identity to the sequence of the mutant virus.

The invention also encompasses the purified polypeptide encoded by the isolated nucleotide sequence of the complete surface antigen gene of the mutant virus, as well as fragments of this sequence. Additionally, the present invention encompasses purified polypeptides having at least 70% similarity, preferably at least 80% similarity, and more preferably at least 90% similarity to the purified polypeptides encoded by the isolated nucleotide sequences, respectively.

Also, the present invention includes an isolated nucleotide sequence which is hybridizable, under moderately stringent conditions, to a nucleotide sequence corresponding to or complementary to the nucleotide sequence of the mutant genome, the nucleotide sequence of the envelope gene, the nucleotide sequence of the HBsAg or the nucleotide sequence encoding the "a" determinant of the mutant virus. A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual", Second Edition (1989), Cold Spring Harbor Laboratory Press, Cold Spring Harbor, N.Y.). The conditions of temperature and ionic strength determine the. "stringency" of the hybridization. "Hybridization" requires that two nucleic acid sequences contain complementary sequences. However, depending on the stringency of the hybridization, mismatches between bases may occur. The appropriate stringency for hybridizing nucleic acids depends on the length of the nucleic acid sequences and the degree of complementarity. Such variables are well known in the art. The greater the degree of similarity or homology between two nucleotide sequences, the greater the value of Tm (i.e., melting temperature) for hybrids of nucleic acids having these sequences. For hybrids of greater than 100 nucleotides in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

Once the nucleotide sequence encoding the amino acid sequence containing the variation (i.e., Thr to Ala at position 123 of the HBsAg) has been isolated, it may then be introduced into either a prokaryotic (e.g., *E. coli*) or eukaryotic host cell (e.g., mammalian cell (such as a HeLa cell or a Chinese hamster ovary cell) or a yeast cell (such as *S. cerevisiae* or *S. carlsbergensis*)) through the use of a vector or construct. The vector or construct of the present invention (e.g., a plasmid, a cosmid, a bacteriophage, etc.) may comprise the nucleotide sequence encoding the mutant protein sequence as well as any promoter which is functional in the host cell and is able to elicit expression of the protein encoded by the nucleotide sequence. The promoter is in operable association with or "operably linked" to the promoter. (A promoter is said to be "operably linked" with a coding sequence if the promoter affects transcription or expression of the coding sequence.) Suitable promoters include, for example, T7, TP1, lactase, and metallothionein and are well-known in the art. The vector may be introduced into the host cell of choice by methods known to those of ordinary skill in the art including, for example, transfections, transformation and electroporation (see Molecular Cloning:

A Laboratory Manual, 2$^{nd}$ ed., Vol. 1–3, ed. Sambrook et al., Cold Spring Harbor Laboratory Press (1989)). The host cell is then cultured under suitable conditions permitting expression of the protein which is then recovered an purified.

It should be noted that expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct than can integrate into the host genome or that autonomously replicates in the host cell. Stable expression of the gene product of interest can be selected for through the use of a selectable marker located on, or transfected with, the expression construct, followed by selection for cells expressing the marker. When stable expression results from integration, the site of the construct's integration may occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

In view of the above, the present invention includes the isolated nucleotide sequence encoding the purified polypeptide of the virus (i.e., the modified "a" determinant having a threonine residue rather than the wildtype alanine residue at position 123 of the amino acid sequence of the HBsAg), the isolated nucleotide sequence of the envelope gene of the mutant virus, the isolated nucleotide sequence encoding the HBsAg of the virus, the isolated nucleotide sequence of the mutant virus, the protein encoded by each sequence, the vector comprising either nucleotide sequence as well as the host cell into which the vector is introduced. It should also be noted that the proteins may be produced either recombinantly, as described above, or synthetically. Further, the proteins may be purified from the virus itself.

The polypeptides or proteins may also be used to develop monoclonal and/or polyclonal antibodies which bind to the immunological epitope(s) of interest of mutant HBV. Methods of producing such antibodies are well known to those of ordinary skill in the art (see, e.g., Kohler and Milstein, *Nature* 256:494 (1975), Mimms et al., *Virology* 176:604–619 (1990), Hammerling et al., *Protein Purification, Principles and Practice,* $2^{nd}$ ed., Springer-Verlag, New York (1984)). Also, one may simply immunize a mammal with the polypeptide or protein of the present invention in order to cause antibody production. Such antibodies may then be recovered. The polypeptide or protein used contains an epitope of the mutant HBV.

As noted above, the present invention also includes methods of detecting antibody to the mutant HBV using the proteins or polypeptides (i.e., antigens), in particular, the HBsAg containing the "a" determinant, described above (see, e.g., U.S. Pat. No. 5,595,739). More specifically, there are two basic types of assays, competitive and non-competitive (e.g., immunometric and sandwich). In both assays, antibody or antigen reagents are covalently or non-covalently attached to the solid phase. Linking agents for covalent attachment are known and may be part of the solid phase or derivatized to it prior to coating. Examples of solid phases used in immunoassays are porous and non-porous materials, latex particles, magnetic particles, microparticles (see published EPO application No. EP 0 425 633), beads, membranes, microtiter wells and plastic tubes. The choice of solid phase material and method of labeling the antigen or antibody reagent are determined based upon desired assay format performance characteristics. For some immunoassays, no label is required. For example, if the antigen is on a detectable particle such as a red blood cell, reactivity can be established based upon agglutination. Alternatively, an antigen-antibody reaction may result in a visible change (e.g., radial immunodiffusion). In most cases, one of the antibody or antigen reagents used in an immunoassay is attached to a signal generating compound or "label". This signal generating compound or "label" is in itself detectable or may be reacted with one or more additional compounds to generate a detectable product. Examples of such signal generating compounds include chromogens, radioisotopes (e.g., 125I, 131I, 32P, 3H, 35S, and 14C), fluorescent compounds (e.g., fluorescein, rhodamine), chemiluminescent compounds, particles (visible or fluorescent), nucleic acids, complexing agents, or catalysts such as enzymes (e.g., alkaline phosphatase, acid phosphatase, horseradish peroxidase, beta-galactosidase, and ribonuclease). In the case of enzyme use, addition of chromo-, fluoro-, or lumogenic substrate results in generation of a detectable signal. Other detection systems such as time-resolved fluorescence, internal-reflection fluorescence, amplification (e.g., polymerase chain reaction) and Raman spectroscopy are also useful.

There are two general formats commonly used to monitor specific antibody titer and type in humans: (1) antigen is presented on a solid phase, as described above, the human biological fluid containing the specific antibodies is allowed to react with the antigen, and then antibody bound to antigen is detected with an anti-human antibody coupled to a signal generating compound and (2) an anti-human antibody is bound to the solid phase, the human biological fluid containing specific antibodies is allowed to react with the bound antibody, and then antigen attached to a signal generating compound is added to detect specific antibody present in the fluid sample. In both formats, the anti-human antibody reagent may recognize all antibody classes, or alternatively; be specific for a particular class or subclass of antibody, depending upon the intended purpose of the assay. These assays formats as well as other known formats are intended to be within the scope of the present invention and are well known to those of ordinary skill in the art.

In view of the above, therefore, the present invention includes a method of detecting antibodies to mutant HBV in a test sample comprising the steps of: (a) contacting the test sample suspected of containing the antibodies with an antigen or protein comprising the modified "a" determinant and thus the Thr to Ala substitution (for example, the HBsAg, the "a" determinant or the full virus); (b) detecting the presence of the complex and thus antibodies present in the test sample. More specifically, the present invention includes a method of detecting antibodies to mutant HBV in a test sample comprising the steps of: (a) contacting the test sample suspected of containing the antibodies with the antigen for a time and under conditions sufficient to allow the formation of antibody/antigen complexes; (b) adding a conjugate to the resulting antibody/antigen complexes for a time and under conditions sufficient to allow the conjugate to bind to the bound antibody, the conjugate comprising an antibody (directed against the protein) attached to a signal generating compound capable of generating a detectable signal; (c) detecting the presence of the antibody which may be present in the test sample by detecting the signal generated by the signal generating compound. A control or calibrator may also be used which binds to the antigen.

Additionally, the present invention includes another method for detecting the presence of antibody which may be present in a test sample. This method comprises the steps of: (a) contacting the test sample suspected of containing antibodies with anti-antibody specific for the antibody in the sample (i.e., anti-mutant HBV antibody or fragment thereof), for a time and under conditions sufficient to allow for formation of anti-antibody/antibody complexes and (b) detecting the presence of antibody which may be present in the test sample. (Such anti-antibodies are commercially available and may be created, for example, by immunizing a mammal with purified mu-chain of the anti-mutant HBV antibody raised again the protein of the present invention or immunogen.)

More specifically, this method may comprise the steps of: (a) contacting the test sample suspected of containing the antibodies (i.e., anti-mutant HBV antibodies) with anti-antibody specific for the antibodies, under time and conditions sufficient to allow the formation of anti-antibody/antibody complexes; (b) adding a conjugate to the resulting anti-antibody/antibody complexes for a time and under conditions sufficient to allow the conjugate to bind to the bound antibody, the conjugate comprising the protein (i.e., antigen comprising the modified "a" determinant) being attached to a signal generating compound capable of generating a detectable signal; and (c) detecting the, presence of the antibodies which may be present in the test sample by detecting the signal generated by the signal generating compound. A control or calibrator may be used which comprises antibody to the anti-antibody.

The present invention also encompasses a third method for detecting the presence of antibody to mutant HBV in a test sample. This method comprises the steps of: (a) contacting the test sample suspected of containing the anti-mutant HBV antibodies with anti-antibody specific for the antibody, under time and conditions sufficient to allow the formation of anti-antibody/antibody complexes; (b) adding protein (i.e., an antigen or polypeptide comprising the modified "a" determinant, for example, the surface antigen) to the resulting anti-antibody/antibody complexes for a time and under conditions sufficient to allow the antigen to bind to the antibody; and (c) adding a conjugate to the resulting anti-antibody/antibody/antigen complexes, the conjugate comprising a composition comprising monoclonal or polyclonal antibody attached to a signal generating compound capable of detecting a detectable signal, the monoclonal or polyclonal antibody being directed against the antigen; and (d) detecting the presence of the antibodies which may be present in the test sample by detecting the signal generated by the signal-generating compound. Again, a control or calibrator may be used which comprises antibody to the anti-antibody.

It should also be noted the one or more of the monoclonal antibodies of the present invention may be used as a competitive probe for the detection of antibodies to the mutant HBV protein of the present invention. For example, a mutant HBV protein of the present invention can be coated on a solid phase. A test sample suspected of containing antibody to the mutant antigen may then be incubated with an indicator reagent comprising a signal-generating compound and at least one monoclonal antibody of the present invention for a time and under conditions sufficient for the formation of antigen/antibody complexes of the test sample and indicator reagent to the solid phase or the indicator reagent to the solid phase. The reduction in binding of the monoclonal antibody to the solid phase can be measured. A measured reduction in the signal as compared to the signal generated from a confirmed negative HBV test sample indicates the presence of anti-HBV antibody in the test sample.

In connection with probes, one may use the nucleic acid sequences of the present invention to synthesize DNA oligomers of about 8–10 nucleotides, or larger, which are useful as hybridization probes in detect the presence of the viral genome in, for example, the sera of subjects suspected of harboring the virus or for screening donated blood for the presence of the virus. The nucleic acid sequences of the present invention also allow for the design and production of mutant HBV specific polypeptides which may be used as diagnostic reagents for the presence of antibodies raised during infection with the virus.

Primers may also be developed using the nucleic acid sequences of the present invention.

It should also be noted that the antibodies of the present invention, or fragments thereof, may be utilized in various diagnostic assays in order to determine the presence of mutant HBV proteins (or nucleic acid sequences corresponding thereto) in a test sample. For example, an antibody directed to one or more of the proteins (i.e., antigens or polypeptides comprising the modified "a" determinant) of the present invention may be added to the test sample for time and under conditions sufficient for the formation of antibody/antigen complexes. If such complexes are detected, then the antigen (i.e., protein) is present in the test sample.

In yet another method, a polyclonal or monoclonal anti-mutant HBV antibody or fragment thereof, or a combination of these antibodies, which has been coated on a solid phase is contacted with a test sample suspected of containing mutant HBV proteins, in order to form a first mixture. This mixture is then incubated for a time and under conditions sufficient to form antigen (i.e., protein)/antibody complexes. An indicator reagent comprising a monoclonal or polyclonal antibody, or fragment thereof, which specifically binds to a mutant HBV region (e.g., the "a" determinant of the virus described herein), or a combination of these antibodies, to which a signal-generating compound has been attached, is then contacted with the antigen/antibody complexes in order to form a second mixture. This second mixture is then incubated for a time and under conditions sufficient for the formation of antibody/antigen/antibody complexes. The presence of mutant HBV protein in the sample and captured on the solid phase is determined by detecting the presence of a measurable signal generated by the signal generating compound. The amount of mutant protein or antigen in the sample is proportional to the signal generated.

Additionally, one may use a different method in order to detect the presence of mutant HBV protein in a test sample. More specifically, a polyclonal or monoclonal anti-mutant HBV antibody (as described above), or a combination thereof, bound to a solid support, the test sample, and an indicator reagent comprising a monoclonal antibody or polyclonal antibody (or fragments thereof) which specifically binds to the mutant HBV antigen (e.g., surface antigen comprising the "a" determinant or the "a" determinant alone), or a combination of these antibodies to which a signal generating compound is attached, are contacted to form a mixture. This mixture is incubated for a time and under conditions sufficient to form antibody/antigen/antibody complexes. Mutant HBV proteins of the present invention and captured on the solid phase are determined by detecting the measurable signal generated by the signal-generating compound. The amount of mutant HBV protein in the test sample is proportional to the signal generated.

It should be noted that one may also detect the presence of antibody and/or antigen to the mutant HBV in a simultaneous assay. More specifically, a test sample is simultaneously contacted with a capture reagent of a first analyte, which comprises a first binding member specific for the first analyte, attached to a solid phase, and a capture reagent of a second analyte, which comprises a first binding member for a second analyte. (A binding member of a pair is defined as a molecule which, through chemical or physical means, specifically binds to the second molecule of the pair.) A mixture is thus formed. This mixture is then incubated for a time and under conditions sufficient to form capture reagent/first analyte and capture reagent/second analyte complexes. These complexes are then contacted with an indicator reagent comprising a member of a binding pair specific for the first analyte labeled with a signal-generating compound and an indicator reagent comprising a member of a binding pair specific for the second analyte labeled with a signal-generating compound. A second mixture is formed. This second mixture is then incubated for a time and under conditions sufficient to form capture reagent/first analyte/indicator reagent complexes and capture reagent/second analyte/indicator reagent complexes. The presence of one or more analytes is determined by detecting a signal generated in connection with the complexes formed on either or both solid phases as an indication of the presence of one of more analytes in the test sample.

While the present invention discloses the use of solid phase diagnostic assays, it is contemplated that the proteins of the present invention may be utilized in non-solid phase diagnostic assays. These assays are well-known to those of ordinary skill in the art and are considered to be within the scope of the present invention.

Additionally, the present invention also includes a vaccine comprising the protein of the present invention and a pharmaceutically acceptable adjuvant (e.g., Freund's adjuvant or Phosphate Buffered Saline (PBS)). Such a vaccine may be administered if one desires to raise antibodies in a mammal. Similarly, the present invention includes a particle which is immunogenic against mutant HBV infection comprising a non-mutant HBV polypeptide having an amino acid sequence capable of forming a particle when the sequence is produced in a eukaryotic host, and an epitope (e.g., the "a" determinant) of the mutant HBV of the present invention.

Kits are also included within the scope of the present invention. More specifically, the present invention includes kits for determining the presence of antibodies. In particular, a kit for determining the presence of antibodies in a test sample comprises a) the protein (i.e., antigen); and b) a conjugate comprising an antibody (directed against the antibody in the test sample) attached to a signal generating compound capable of generating a detectable signal. The kit may also contain a control or calibrator.

The present invention also includes another type of kit for detecting antibodies in a test sample. The kit may comprise a) an anti-antibody specific for the antibody in the test sample (i.e., that produced in response to the mutant HBV), and b) the protein (i.e., the "a" determinant containing the Thr to Ala substitution or a polypeptide such as the surface antigen comprising the "a" determinant). A control or calibrator comprising a reagent which binds to the protein may also be included. More specifically, the kit may comprise a) an anti-antibody specific for the antibody in the sample, and b) a conjugate comprising the protein, the conjugate being attached to a signal-generating compound capable of generating a detectable signal. Again, the kit may also comprise a control of calibrator comprising a reagent which binds to the protein.

In addition, the isolated nucleotide sequences of the present invention, as well as the related sequences described above with respect to sequence identity, may be used in order to create primers and probes. The probes may be used to detect nucleic acids in test samples, and the primers may be used for amplification purposes.

The design of such probes, for optimization in assays, in well within the knowledge of one of ordinary skill in the art. Generally, nucleic acid probes are developed from non-conserved regions when maximum specificity is desired, and nucleic acid probes are developed from conserved regions when assaying for nucleotide regions that are closely related to, for example, different members of a multi-gene family or in related species.

The probes (nucleotide sequences) of the present invention may be used, for example, to discover other antisense oligonucleotides related to those of the present invention. Thus, the probes would hybridize to portions of the Chk1 nucleotide sequence which may then be utilized, for example, for therapeutic purposes.

Primers may also be developed, using the nucleic acid sequences of the present invention, for utilization in the polymerase chain reaction (PCR) (see U.S. Pat. No. 4,683,195 and U.S. Pat. No. 4,683,202). PCR is a technique for amplifying a desired nucleic acid sequence contained in a nucleic acid or mixture thereof. The primers are each extended by a polymerase using the target nucleic acid as a template. The extension products become target sequences, following dissociation from the original target strand. New primers are then hybridized and extended by a polymerase, and the cycle is repeated in order to increase the number of target sequence molecules.

The present invention also encompasses a tissue culture-grown cell infected with the mutant HBV as well as the isolated mutant hepatitis B virus itself. Additionally, the present invention includes an immunogenic composition comprising the virus wherein the virus is attenuated or inactivated.

The present invention may be illustrated by the use of the following non-limiting examples:

EXAMPLE I

Isolation of Thr 123 to Ala HBsAg Mutant

DNA Isolation.

A 100 ul aliquot of the French sample identified as 990525169(and which had been deposited with the Agence Française de Sécurité Sanitaire des Produits de Santé, 6 rue Alexandre Cabanel, 75739 Paris Cedex 15, France) was thawed and 150 ul of freshly prepared Digest Mixture (16.67 mM Tris pH 8.0, 16.67 mM EDTA pH 8.00, 0.83% SDS, 1.67 mg/ml Proteinase K) (Sigma Chemical Co., St. Louis, Mo.) was added in a 1.6 ml siliconized microfuge tube. The sample was vortexed and incubated for 2 hours at 60° C., then microfuged (12,000 rpm in 3743 Biofuge rotor (Baxter Scientific Products, Baxter Park, Ill.) for 10 min. The supernatant was removed and 250 ul of Phenol/Chloroform/Isoamyl Alcohol (25/24/1) [Sigma P-3803] was added and the mixture was vortexed vigorously for 30 sec., then again microfuged for 10 min. The upper aqueous phase was removed while avoiding the interface material and the extraction was repeated. DNA was precipitated by adding 0.1 volume of 3M sodium acetate buffer [Sigma S-7899] and 2 volumes of absolute ethanol [McCormick 6505-00-105-0000]. The sample was vortexed and held at −20° C. for at least 30 min., and then microfuged for 15 min. The supernatant was removed being careful not to disturb the pellet area. The pellet was washed with 250 ul of 70% ethanol then centrifuged for 5 min. The wash step was again repeated, then the pellet was allowed to air dry for approximately 5 min. at room temperature. The pellet was resuspended in 40 ul of water [Sigma W-4502] by using the pipette tip to resuspend the pellet area and vortexing vigorously. The microfuge tube was labelled with sample ID# and date and stored at 4° C.

PCR Amplification.

A nested PCR amplification of the full surface antigen gene (preS1/preS2/S) was performed using the Perkin Elmer GeneAmp kit [N808-0143] (Norwalk, Conn.) and a Perkin Elmer 9600 thermocycler. In the first round amplifcation, 5 ul of extracted DNA was amplified using HBV primers 2844F and 883R with the following conditions:

| PCR 1 rxn. | |
| --- | --- |
| Primer1 | 1.25 ul |
| Primer2 | 1.25 ul |
| 10X Buffer | 2.5 ul |
| MgCl$_2$ solution | 2.0 ul |
| dNTP mixture | 2.5 ul |
| H2O | 10.4 ul |
| Taq | 0.125 ul |
| | 20 ul per tube |

Sample = 5 ul DNA, Total volume = 25 ul.

The above mixture was amplified in a PE9600 using the following method:

(94C, 2 m/94C, 30s-50C, 30s-72C, 60s[10 cycles]/95C, 30s-60C, 30s-72C, 60s[30 cycles]/ 72C, 10 m/4C soak).

In the second round amplification, 1 ul of the PCR 1 rxn. mixture was further amplified using HBV primers 2822F and 850R under the following conditions:

| PCR 2 rxn. | |
| --- | --- |
| Primer 3 | 1.25 ul |
| Primer 4 | 1.25 ul |
| 10X Buffer | 2.5 ul |
| MgCl$_2$ solution | 2.0 ul |
| dNTP mixture | 2.5 ul |
| H$_2$O | 14.4 ul |
| Taq | 0.125 ul |
| | 24 ul per tube |

Sample = 1 ul PCR1 rxn.., Total volume = 25 ul.

The PCR 2 mixture was amplified in a PE9600 using the same method:

(94C, 2m/94C, 30s-50C, 30s-72C, 60s[10 cycles]/95C, 30s-60C, 30s-72C, 60s[30 cycles]/72C, 10 m/4C soak).

The PCR 2 product was then electrophoresed on a 11% agarose gel with appropriate sizing standards. The major band corresponding to approximately 1,250 base pairs was excised and isolated using a QIAquick gel extraction kit [28704] (Qiagen Inc., Chatsworth, Calif.).

DNA Sequencing.

The purified PCR product was sequenced on an ABI 373 Automated DNA Sequencer using nine HBV primers; 2822F, 3135F, 56F, 251R, 448F, 471R, 623F, 714R, and 850R. The nine sequence contigs were assembled into one sequence using Sequencer software. The sample was shown to contain a HBV subtype ayw2, genotype D sequence in which the following three substitutions were found:

1.) Thr to Ala 123 (affects H166 epitope)
2.) Trp to Leu 199 (outside “a” determinant)
3.) Ser to Thr 207 (outside “a” determinant)

The invention claimed is:

1. An isolated mutant hepatitis B surface antigen (HBsAg) protein comprising the amino acid sequence of SEQ ID NO:2.

2. An immunogenic composition comprising said isolated mutant HBsAg protein of claim 1.

3. A kit for determining the presence of mutant hepatitis B virus antigen or antibody comprising a container containing said isolated mutant HBsAg protein of claim 1.

* * * * *

SEQUENCE LISTING

```
<160> NUMBER OF SEQ ID NOS: 8

<210> SEQ ID NO 1
<211> LENGTH: 1181
<212> TYPE: DNA
<213> ORGANISM: Hepatitis B Virus

<400> SEQUENCE: 1
atggggcaga atctttccac cagcaatcct ctgggattct ttcccgacca ccagttggat     60
ccagccttca gagcaaacac caacaatcca gattgggact tcaatcccaa caaggacacc    120
tggccagacg ccaacaaggt aggagctgga gcattcggac tggggttcac cccaccgcac    180
ggaggccttt tggggtggag ccctcaggct cagggcataa cacaaacctt gccagcaaat    240
ccgcctcctg cttccaccaa tcgccagtca ggaaggcagc ctaccccgct gtctccacct    300
ttgagaaaca ctcatcctca agccatgcag tggaactcca caactttcca ccaaactctg    360
caagatccca gagtgagagg tctgtatttc cctgctggtg gctccagttc aggaacagta    420
aaccctgttc cgactactgt ctctcccata tcgtcaatct tctcgaggat tggggaccct    480
gcgcggaaca tggagaacat cacatcagga ttcctaggac ccctgctcgt gttacaggcg    540
```

-continued

```
gggttttttct tgttgacaag aatcctcaca ataccgcaga gtctagactc gtggtggact    600
tctctcaatt ttctaggggg aactaccgtg tgtcttggcc aaaattcgca gtccccaacc    660
tccaatcact caccaacctc ctgtcctcca acttgtcctg gttatcgctg gatgtgtctg    720
cggcgtttta tcatcttcct cttcatcctg ctgctatgcc tcatcttctt gttggttctt    780
ctggactatc aagtatgtt gcccgtttgt cctctaattc caggatcttc aaccaccagc    840
acgggaccat gcagagcctg cacgactcct gctcaaggaa cctctatgta tccctcctgt    900
tgctgtacaa aaccttcgga tggaaactgc acctgtattc ccatcccatc atcctgggct    960
ttcggaaaat tcctatggga gtgggcctca gcccgtttct cctggctcag tttactagtg   1020
ccatttgttc agtggttcgt agggctttcc cccactgttt ggctttcagt tatatggatg   1080
atgttgtact gggggccaag tctgtacacc atcttgagtc ccttttttacc gctgttacca   1140 attttctttt gtctttgggt atacatttaa accctaataa a                         1181
```

<210> SEQ ID NO 2
<211> LENGTH: 389
<212> TYPE: PRT
<213> ORGANISM: Hepatitis B Virus

<400> SEQUENCE: 2

```
Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Asn Asn Pro Asp Trp
                20                  25                  30

Asp Phe Asn Pro Asn Lys Asp Thr Trp Pro Asp Ala Asn Lys Val Gly
            35                  40                  45

Ala Gly Ala Phe Gly Leu Gly Phe Thr Pro Pro His Gly Gly Leu Leu
        50                  55                  60

Gly Trp Ser Pro Gln Ala Gln Gly Ile Thr Gln Thr Leu Pro Ala Asn
65                  70                  75                  80

Pro Pro Pro Ala Ser Thr Asn Arg Gln Ser Gly Arg Gln Pro Thr Pro
                85                  90                  95

Leu Ser Pro Pro Leu Arg Asn Thr His Pro Gln Ala Met Gln Trp Asn
                100                 105                 110

Ser Thr Thr Phe His Gln Thr Leu Gln Asp Pro Arg Val Arg Gly Leu
            115                 120                 125

Tyr Phe Pro Ala Gly Gly Ser Ser Gly Thr Val Asn Pro Val Pro
        130                 135                 140

Thr Thr Val Ser Pro Ile Ser Ser Ile Phe Ser Arg Ile Gly Asp Pro
145                 150                 155                 160

Ala Arg Asn Met Glu Asn Ile Thr Ser Gly Phe Leu Gly Pro Leu Leu
                165                 170                 175

Val Leu Gln Ala Gly Phe Phe Leu Leu Thr Arg Ile Leu Thr Ile Pro
            180                 185                 190

Gln Ser Leu Asp Ser Trp Trp Thr Ser Leu Asn Phe Leu Gly Gly Thr
        195                 200                 205

Thr Val Cys Leu Gly Gln Asn Ser Gln Ser Pro Thr Ser Asn His Ser
    210                 215                 220

Pro Thr Ser Cys Pro Pro Thr Cys Pro Gly Tyr Arg Trp Met Cys Leu
225                 230                 235                 240

Arg Arg Phe Ile Ile Phe Leu Phe Ile Leu Leu Cys Leu Ile Phe
                245                 250                 255

Leu Leu Val Leu Leu Asp Tyr Gln Gly Met Leu Pro Val Cys Pro Leu
```

-continued

```
                260                 265                 270
Ile Pro Gly Ser Ser Thr Thr Ser Thr Gly Pro Cys Arg Ala Cys Thr
            275                 280                 285
Thr Pro Ala Gln Gly Thr Ser Met Tyr Pro Ser Cys Cys Cys Thr Lys
        290                 295                 300
Pro Ser Asp Gly Asn Cys Thr Cys Ile Pro Ile Pro Ser Ser Trp Ala
305                 310                 315                 320
Phe Gly Lys Phe Leu Trp Glu Trp Ala Ser Ala Arg Phe Ser Trp Leu
                325                 330                 335
Ser Leu Leu Val Pro Phe Val Gln Trp Phe Val Gly Leu Ser Pro Thr
            340                 345                 350
Val Trp Leu Ser Val Ile Trp Met Met Leu Tyr Trp Gly Pro Ser Leu
        355                 360                 365
Tyr Thr Ile Leu Ser Pro Phe Leu Pro Leu Leu Pro Ile Phe Phe Cys
    370                 375                 380
Leu Trp Val Tyr Ile
385

<210> SEQ ID NO 3
<211> LENGTH: 681
<212> TYPE: DNA
<213> ORGANISM: Hepatitis B Virus

<400> SEQUENCE: 3
atggagaaca tcacatcagg attcctagga ccctgctcg tgttacaggc ggggttttc      60 tggttgacaa gaatcctcac aataccgcag agtctagact cgtggtggac ttctctcaat    120
tttctagggg gaactaccgt gtgtcttggc caaaattcgc agtccccaac ctccaatcac    180
tcaccaacct cctgtcctcc aacttgtcct ggttatcgct ggatgtgtct gcggcgtttt    240
atcatcttcc tcttcatcct gctgctatgc ctcatcttct tgttggttct tctggactat    300
caaggtatgt tgcccgtttg tcctctaatt ccaggatcat caaccaccag cacgggaccc    360
tgcagaacct gcacgactcc tgctcaagga acctctatgt atccctcctg ttgctgtaca    420
aaaccttcgg atggaaactg cacctgtatt cccatcccat catcctgggc tttcggaaaa    480
ttcctatggg agtgggcctc agcccgtttc tcttggctca gtttactagt gccatttgtt    540
cagtggttcg tagggctttc ccccactgtt tggctttcag ttatatggat gatgtggtat    600
tgggggccaa gtctgtacag catcttgagt cccttttac cgctgttacc aattttcttt    660
tgtctttggg tatacattta a                                              681

<210> SEQ ID NO 4
<211> LENGTH: 182
<212> TYPE: DNA
<213> ORGANISM: Hepatitis B Virus
<220> FEATURE:
<223> OTHER INFORMATION: "a" Determinant for the Hepatitis B Virus
      Strain

<400> SEQUENCE: 4
tatcaaggta tgttgcccgt tgtcctcta attccaggat cttcaaccac cagcacggga      60
ccatgcagac tgcacgact cctgctcaag gaacctctat gtatccctcc tgttgctgta    120
caaaaccttc ggatggaaac tgcacctgta ttcccatccc atcatcctgg ctttcggaa    180 aa                                                                   182

<210> SEQ ID NO 5
```

-continued

```
<211> LENGTH: 61
<212> TYPE: PRT
<213> ORGANISM: Hepatitis B Virus
<220> FEATURE:
<223> OTHER INFORMATION: "a" Determinant for the mutant Hepatitis B
      Virus strain

<400> SEQUENCE: 5
```

Tyr Gln Gly Met Leu Pro Val Cys Pro Leu Ile Pro Gly Ser Ser Thr
1               5                   10                  15

Thr Ser Thr Gly Pro Cys Arg Ala Cys Thr Thr Pro Ala Gln Gly Thr
            20                  25                  30

Ser Met Tyr Pro Ser Cys Cys Cys Thr Lys Pro Ser Asp Gly Asn Cys
        35                  40                  45

Thr Cys Ile Pro Ile Pro Ser Ser Trp Ala Phe Gly Lys
    50                  55                  60

```
<210> SEQ ID NO 6
<211> LENGTH: 690
<212> TYPE: DNA
<213> ORGANISM: Hepatitis B Virus
<220> FEATURE:
<223> OTHER INFORMATION: Mutant Hepatitis B Virus Strain

<400> SEQUENCE: 6
```

| | | | | | |
|---|---|---|---|---|---|
| gcgcggaaca | tggagaacat | cacatcagga | ttcctaggac | ccctgctcgt | gttacaggcg | 60 |
| gggttttttct | tgttgacaag | aatcctcaca | ataccgcaga | gtctagactc | gtggtggact | 120 |
| tctctcaatt | ttctaggggg | aactaccgtg | tgtcttggcc | aaaattcgca | gtccccaacc | 180 |
| tccaatcact | caccaacctc | ctgtcctcca | acttgtcctg | gttatcgctg | gatgtgtctg | 240 |
| cggcgtttta | tcatcttcct | cttcatcctg | ctgctatgcc | tcatcttctt | gttggttctt | 300 |
| ctggactatc | aaggtatgtt | gcccgtttgt | cctctaattc | caggatcttc | aaccaccagc | 360 |
| acgggaccat | gcagagcctg | cacgactcct | gctcaaggaa | cctctatgta | tcccctcctgt | 420 |
| tgctgtacaa | aaccttcgga | tggaaactgc | acctgtattc | ccatcccatc | atcctgggct | 480 |
| ttcggaaaat | tcctatggga | gtgggcctca | gcccgtttct | cctggctcag | tttactagtg | 540 |
| ccatttgttc | agtggttcgt | agggctttcc | cccactgttt | ggctttcagt | tatatggatg | 600 |
| atgttgtact | gggggccaag | tctgtacacc | atcttgagtc | ccttttttacc | gctgttacca | 660 |
| attttctttt | gtctttgggt | atacatttaa | | | | 690 |

```
<210> SEQ ID NO 7
<211> LENGTH: 690
<212> TYPE: DNA
<213> ORGANISM: Hepatitis B Virus

<400> SEQUENCE: 7
```

| | | | | | |
|---|---|---|---|---|---|
| gcgctgaaca | tggagaacat | cacatcagga | ttcctaggac | ccctgctcgt | gttacaggcg | 60 |
| gggttttttct | tgttgacaag | aatcctcaca | ataccgcaga | gtctagactc | gtggtggact | 120 |
| tctctcaatt | ttctaggggg | aactaccgtg | tgtcttggcc | aaaattcgca | gtccccaacc | 180 |
| tccaatcact | caccaacctc | ctgtcctcca | acttgtcctg | gttatcgctg | gatgtgtctg | 240 |
| cggcgtttta | tcatcttcct | cttcatcctg | ctgctatgcc | tcatcttctt | gttggttctt | 300 |
| ctggactatc | aaggtatgtt | gcccgtttgt | cctctaattc | caggatcatc | aaccaccagc | 360 |
| acgggaccct | gcaggacctg | cacgactcct | gctcaaggaa | cctctatgta | tcccctcctgt | 420 |
| tgctgtacaa | aaccttcgga | tggaaactgc | acctgtattc | ccatcccatc | atcctgggct | 480 |

-continued

```
ttcggaaaat tcctatggga gtgggcctca gcccgtttct cttggctcag tttactagtg      540
ccatttgttc agtggttcgt agggcttttcc cccactgttt ggctttcagt tatatggatg     600
atgtggtatt gggggccaag tctgtacagc atcttgagtc cctttttacc gctgttacca     660 atttctttt gtctttgggt atacatttaa                                        690
```

<210> SEQ ID NO 8
<211> LENGTH: 229
<212> TYPE: PRT
<213> ORGANISM: Hepatitis B Virus
<220> FEATURE:
<221> NAME/KEY: VARIANT
<222> LOCATION: (126)...(126)
<223> OTHER INFORMATION: Xaa = A or T at position 126
<220> FEATURE:
<221> NAME/KEY: VARIANT
<222> LOCATION: (202)...(202)
<223> OTHER INFORMATION: Xaa = L or W at position 202
<220> FEATURE:
<221> NAME/KEY: VARIANT
<222> LOCATION: (210)...(210)
<223> OTHER INFORMATION: Xaa = T or S at position 210

<400> SEQUENCE: 8

```
Ala Arg Asn Met Glu Asn Ile Thr Ser Gly Phe Leu Gly Pro Leu Leu
 1               5                  10                  15

Val Leu Gln Ala Gly Phe Phe Leu Leu Thr Arg Ile Leu Thr Ile Pro
            20                  25                  30

Gln Ser Leu Asp Ser Trp Trp Thr Ser Leu Asn Phe Leu Gly Gly Thr
        35                  40                  45

Thr Val Cys Leu Gly Gln Asn Ser Gln Ser Pro Thr Ser Asn His Ser
    50                  55                  60

Pro Thr Ser Cys Pro Pro Thr Cys Pro Gly Tyr Arg Trp Met Cys Leu
65                  70                  75                  80

Arg Arg Phe Ile Ile Phe Leu Phe Ile Leu Leu Leu Cys Leu Ile Phe
                85                  90                  95

Leu Leu Val Leu Leu Asp Tyr Gln Gly Met Leu Pro Val Cys Pro Leu
            100                 105                 110

Ile Pro Gly Ser Ser Thr Thr Ser Thr Gly Pro Cys Arg Xaa Cys Thr
        115                 120                 125

Thr Pro Ala Gln Gly Thr Ser Met Tyr Pro Ser Cys Cys Cys Thr Lys
    130                 135                 140

Pro Ser Asp Gly Asn Cys Thr Cys Ile Pro Ile Pro Ser Ser Trp Ala
145                 150                 155                 160

Phe Gly Lys Phe Leu Trp Glu Trp Ala Ser Ala Arg Phe Ser Trp Leu
                165                 170                 175

Ser Leu Leu Val Pro Phe Val Gln Trp Phe Val Gly Leu Ser Pro Thr
            180                 185                 190

Val Trp Leu Ser Val Ile Trp Met Met Xaa Tyr Trp Gly Pro Ser Leu
        195                 200                 205

Tyr Xaa Ile Leu Ser Pro Phe Leu Pro Leu Pro Ile Phe Phe Cys
    210                 215                 220

Leu Trp Val Tyr Ile
225
```